United States Patent
Nakajima et al.

(10) Patent No.: US 10,435,228 B2
(45) Date of Patent: Oct. 8, 2019

(54) TWO-LIQUID MIXING-TYPE AEROSOL PRODUCT

(71) Applicant: Toyo Aerosol Industry Co., Ltd., Tokyo (JP)

(72) Inventors: Yasutomo Nakajima, Tokyo (JP); Makoto Tsubouchi, Tokyo (JP); Hokuto Kamijyo, Tokyo (JP); Tomoyuki Niinomi, Tokyo (JP); Remi Ikeda, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/552,711

(22) PCT Filed: Feb. 23, 2016

(86) PCT No.: PCT/JP2016/055160
§ 371 (c)(1),
(2) Date: Aug. 22, 2017

(87) PCT Pub. No.: WO2016/136703
PCT Pub. Date: Sep. 1, 2016

(65) Prior Publication Data
US 2018/0029781 A1 Feb. 1, 2018

(30) Foreign Application Priority Data
Feb. 27, 2015 (JP) ................................. 2015-038110

(51) Int. Cl.
*B65D 83/68* (2006.01)
*A45D 34/04* (2006.01)
(Continued)

(52) U.S. Cl.
CPC ........... *B65D 83/682* (2013.01); *A45D 34/04* (2013.01); *A61K 8/02* (2013.01); *A61K 8/046* (2013.01);
(Continued)

(58) Field of Classification Search
CPC .................. B65D 83/682; B65D 83/62; B65D 83/68–687; B65D 83/14–759;
(Continued)

(56) References Cited

U.S. PATENT DOCUMENTS 6,168,335 B1   1/2001   Mears et al.
7,036,685 B1   5/2006   Green
(Continued)

FOREIGN PATENT DOCUMENTS

EP   0885000 A2   12/1998
JP   2000319643 A   11/2000
(Continued)

OTHER PUBLICATIONS

International Search Report dated Apr. 5, 2016 for PCT/JP2016/055160.
(Continued)

*Primary Examiner* — Christopher S Kim
*Assistant Examiner* — Juan C Barrera
(74) *Attorney, Agent, or Firm* — Lucas & Mercanti, LLP

(57) ABSTRACT

The present invention has as its object the provision of a two-liquid mixing-type aerosol product having high formulation stability, being capable of easily forming a discharge material having a desired composition, and providing comfort during use when it is applied to the human body.

A two-liquid mixing-type aerosol product of the present invention has a double-structure container including a propellant filling space and two liquid concentrate filling spaces and having a discharging mechanism for simultaneously (Continued)

discharging the contents filled in the two liquid concentrate filling spaces. The propellant filling space is filled with a propellant composed of a compressed gas. A first liquid concentrate filling space is filled with a first liquid concentrate composition having a viscosity of 1 to 1000 mPa·s at a temperature of 20° C. A second liquid concentrate filling space is filled with a second liquid concentrate composition having a viscosity of 1 to 1000 mPa·s at a temperature of 20° C. The discharging mechanism has a function for breaking the first liquid concentrate composition and the second liquid concentrate composition down into fine droplets and discharging these liquid concentrate compositions as mists.

7 Claims, 1 Drawing Sheet

(51) Int. Cl.

| | |
|---|---|
| *A61Q 17/04* | (2006.01) |
| *A61Q 19/00* | (2006.01) |
| *A61K 8/02* | (2006.01) |
| *A61K 8/9794* | (2017.01) |
| *A61K 8/9789* | (2017.01) |
| *A61K 8/04* | (2006.01) |
| *A61K 8/31* | (2006.01) |
| *A61K 8/34* | (2006.01) |
| *A61K 8/362* | (2006.01) |
| *A61K 8/37* | (2006.01) |
| *A61K 8/58* | (2006.01) |
| *A61K 8/67* | (2006.01) |
| *A61K 8/73* | (2006.01) |
| *A61K 8/891* | (2006.01) |
| *A61Q 19/02* | (2006.01) |
| *B65D 83/62* | (2006.01) |
| *A61M 11/00* | (2006.01) |

(52) U.S. Cl.

CPC .................. *A61K 8/31* (2013.01); *A61K 8/34* (2013.01); *A61K 8/345* (2013.01); *A61K 8/362* (2013.01); *A61K 8/37* (2013.01); *A61K 8/585* (2013.01); *A61K 8/676* (2013.01); *A61K 8/678* (2013.01); *A61K 8/735* (2013.01); *A61K 8/891* (2013.01); *A61K 8/9789* (2017.08); *A61K 8/9794* (2017.08); *A61Q 17/04* (2013.01); *A61Q 19/00* (2013.01); *A61Q 19/02* (2013.01); *B65D 83/62* (2013.01); *B65D 83/68* (2013.01); *A45D 2200/057* (2013.01); *A45D 2200/058* (2013.01); *A61K 2800/87* (2013.01); *A61K 2800/882* (2013.01); *A61M 11/006* (2014.02)

(58) Field of Classification Search

CPC .............. A45D 34/04; A45D 2200/057; A45D 2200/058; A45D 34/00–06; B05B 1/3405; B05B 7/00–32; A61K 8/9794; A61K 8/9789; A61K 8/02; A61K 8/046; A61K 8/31; A61K 8/34; A61K 8/345; A61K 8/362; A61K 8/37; A61K 8/585; A61K 8/676; A61K 8/678; A61K 8/735; A61K 8/891; A61Q 17/04; A61Q 19/02; A61Q 19/00–10; A61Q 19/08; A61Q 13/00; A61Q 17/00; A61Q 19/007; A61Q 19/008; A61Q 5/00; A61Q 5/006; A61Q 7/00; A61M 11/006; B01F 2003/0842; B01F 3/0807; B01F 5/0256; B01F 13/0069; B01F 13/0074; B01F 2003/0838; B01F 2003/0834; B01F 5/10

USPC ................................ 239/398, 407, 408, 410

See application file for complete search history.

(56) References Cited

U.S. PATENT DOCUMENTS

| | | | | |
|---|---|---|---|---|
| 7,455,195 | B2 | 11/2008 | Mekata | |
| 7,798,366 | B2 | 9/2010 | Hoshino | |
| 9,475,636 | B2 | 10/2016 | Mekata et al. | |
| 9,828,170 | B2 | 11/2017 | Nomura et al. | |
| 2003/0215416 | A1 | 11/2003 | Hirano | |
| 2007/0241133 | A1* | 10/2007 | Smith | B05B 11/0078 222/129 |
| 2009/0108021 | A1 | 4/2009 | Hansen et al. | |
| 2011/0215113 | A1* | 9/2011 | Hansen | B65D 83/202 222/136 |
| 2012/0126034 | A1 | 5/2012 | Nolen | |
| 2013/0270294 | A1* | 10/2013 | Shibata | B65D 83/48 222/94 |
| 2014/0246515 | A1 | 9/2014 | Nakajima | |
| 2016/0128915 | A1 | 5/2016 | Konno et al. | |

FOREIGN PATENT DOCUMENTS

| | | | |
|---|---|---|---|
| JP | 2001026526 | A | 1/2001 |
| JP | 2004161292 | A | 6/2004 |
| JP | 2010069421 | A | 4/2010 |
| JP | 2010235174 | A | 10/2010 |
| JP | 2012036102 | A | 2/2012 |
| JP | 2012090966 | A | 5/2012 |
| JP | 2012-229318 | A | 11/2012 |
| JP | 5390729 | B1 | 10/2013 |
| JP | 2014237621 | A | 12/2014 |
| JP | 2015013836 | A | 1/2015 |
| WO | 2014/208735 | A1 | 12/2014 |

OTHER PUBLICATIONS

Extended European Search Report dated Feb. 9, 2018 from the corresponding European Application No. 16755447.6.

Office Action dated Apr. 4, 2018 from the corresponding U.S. Appl. No. 15/552,741.

Extended European Search Report dated Jan. 30, 2018 from corresponding European Application No. 16755448.4.

International Search Report dated Apr. 5, 2016 for PCT/JP2016/055161 and English translation.

International Preliminary Report on Patentability dated Jul. 12, 2016 for PCT/JP2016/067010 and English translation.

* cited by examiner

TWO-LIQUID MIXING-TYPE AEROSOL PRODUCT

CROSS REFERENCE TO RELATED APPLICATION

This Application is a 371 of PCT/JP2016/055160 filed on Feb. 23, 2016 which, in turn, claimed the priority of Japanese PCT Patent Application No. 2015-038110 filed Feb. 27, 2015, both applications are incorporated herein by reference.

TECHNICAL FIELD

The present invention relates to two-liquid mixing-type aerosol products, and in particular, to a two-liquid mixing-type aerosol product that delivers a discharge material as a mist.

BACKGROUND ART

In the related art, liquid compositions used as, for example, daily necessaries, food, and products for the human body such as cosmetic preparations contain two liquids immiscible with each other, for example, water and liquid oil, ethanol and liquid paraffin, or liquid paraffin and a certain ester compound, as media for active ingredients.

Specific examples of certain liquid cosmetic formulations include those constituted by a water-based liquid composition containing a water-soluble component as an active ingredient in a medium of water, and an oil-based liquid composition containing an oil-soluble component as an active ingredient in a medium of a liquid oil immiscible with water. Such liquid cosmetic formulations are formed as an emulsion composition by the action of a surfactant.

However, since such a liquid cosmetic formulation undergoes separation between the aqueous phase (water-based liquid composition) and the oil phase (oil-based liquid composition) during a long-term storage, the liquid cosmetic formulation needs to be emulsified when it is applied. Furthermore, the surfactant may cause skin irritation at application sites or the like. In addition to these problems, a particular problem may arise depending on the intended use, specifically, the type of active ingredient used.

For example, in liquid cosmetic formulations for beauty products, vitamin C and vitamin C derivatives which are active ingredients for skin whitening are water-soluble substances, whereas vitamin E and vitamin E derivatives which are active ingredients for antioxidation are oil-soluble substances. It is thus difficult to maintain the stability (formulation stability) of these two active ingredients in the emulsion composition.

For example, liquid cosmetic formulations for sunscreens need to contain a large amount of oil medium for dissolving an ultraviolet absorbing component because such liquid cosmetic formulations for sunscreens contain an ultraviolet absorbing component as an active ingredient. When water is added to improve feeling during use, a large amount of surfactant needs to be added. A large amount of surfactant tends to cause skin irritation and sticky feeling instead of comfort during use at application sites or the like.

As a cosmetic preparation composed of a liquid cosmetic formulation, there is provided a preparation placed in a container and containing a water-based liquid composition and an oil-based liquid composition with these liquid compositions separated from each other.

Before application to an application site, however, such a cosmetic preparation requires mixing the water-based liquid composition and the oil-based liquid composition well on the palm after taken from the container. This process is burdensome. In addition to this problem, there is another problem in that sticky feeling is caused instead of comfort during use.

CITATION LIST

Patent Literature

Patent Literature 1: Japanese Patent Application Laid-Open No. 2001-26526
Patent Literature 2: Japanese Patent Application Laid-Open No. 2012-036102

SUMMARY OF INVENTION

Technical Problem

The present invention has been made in view of the foregoing circumstances and has as its object the provision of a two-liquid mixing-type aerosol product of an aerosol dispenser having high formulation stability, being capable of easily forming a discharge material having a desired composition, and providing comfort during use when it is applied to the human body.

Solution to Problem

A two-liquid mixing-type aerosol product of the present invention has a double-structure container including a propellant filling space and two independent liquid concentrate filling spaces and having a discharging mechanism for simultaneously discharging contents filled in the two liquid concentrate filling spaces, the propellant filling space in the double-structure container is filled with a propellant composed of a compressed gas, a first liquid concentrate filling space in the double-structure container is filled with a first liquid concentrate composition, and a second liquid concentrate filling space in the double-structure container is filled with a second liquid concentrate composition, the first liquid concentrate composition is a liquid that contains a first component in a first medium with the first component capable of being dissolved in the first medium, the second liquid concentrate composition is a liquid that contains a second component in a second medium with the second medium capable of being dissolved in the second medium and that is immiscible with the first liquid concentrate composition, the first liquid concentrate composition and the second liquid concentrate composition each have a viscosity from 1 to 1000 mPa·s at a temperature of 20° C., and the discharging mechanism has a function for breaking the first liquid concentrate composition and the second liquid concentrate composition down into fine droplets and discharging the liquid concentrate compositions as mists.

In the two-liquid mixing-type aerosol product of the present invention, the first liquid concentrate composition may preferably contain the first component composed of an oil-soluble component or an oil-insoluble component in the first medium composed of an oil medium or a non-oil medium, and the second liquid concentrate composition may preferably be an oil product containing the second component composed of an oil-soluble component in the second medium composed of an oil medium.

In the two-liquid mixing-type aerosol product of the present invention, the mixing ratio of the first liquid concentrate composition to the second liquid concentrate composition (the mass of the first liquid concentrate composition:the mass of the second liquid concentrate composition) discharged from the discharging mechanism may preferably be from 0.8:1.2 to 1.2:0.8.

In the two-liquid mixing-type aerosol product of the present invention, the oil medium may preferably be at least one selected from the group consisting of a hydrocarbon compound, an ester compound, a silicone compound, an oil or fat, and a higher alcohol.

In the two-liquid mixing-type aerosol product of the present invention, the oil-insoluble component may preferably be at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an anti-pruritic component, a hair growth component and a deodorant component.

In the two-liquid mixing-type aerosol product of the present invention, the oil-soluble component may preferably be at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an anti-pruritic component, a hair growth component and a deodorant component.

In the two-liquid mixing-type aerosol product of the present invention, the discharging mechanism may preferably have a swirl passage through which the first liquid concentrate composition and the second liquid concentrate composition to be discharged are passed and broken down into fine droplets.

The two-liquid mixing-type aerosol product of the present invention may preferably be used for the human body.

Advantageous Effects of Invention

The two-liquid mixing-type aerosol product of the present invention has a double-structure container including a discharging mechanism for simultaneously discharging the contents filled in two liquid concentrate filling spaces as mists. One of the two liquid concentrate filling spaces is filled with a first liquid concentrate composition having a particular viscosity, whereas the other is filled with a second liquid concentrate composition having a particular viscosity and being immiscible with the first liquid concentrate composition. Therefore, there is no need to use a surfactant for emulsifying the first liquid concentrate composition and the second liquid concentrate composition. The first liquid concentrate composition and the second liquid concentrate composition both have a large degree of freedom in formulation design, and high formulation stability is obtained. In addition, the first liquid concentrate composition and the second liquid concentrate composition can always be mixed at a constant quantitative ratio, and the discharge material can be applied to an application site thinly and uniformly.

Therefore, the two-liquid mixing-type aerosol product of the present invention has high formulation stability and easily enables a discharge material composed of a mixture containing the first liquid concentrate composition and the second liquid concentrate composition at a desired ratio to be uniformly applied to an application site in a desired amount. In the case of application to the human body, the two-liquid mixing-type aerosol product of the present invention can prevent or reduce occurrence of sticky feeling caused by addition of a surfactant and can thus provide comfort during use.

DESCRIPTION OF EMBODIMENTS

Figure 1:
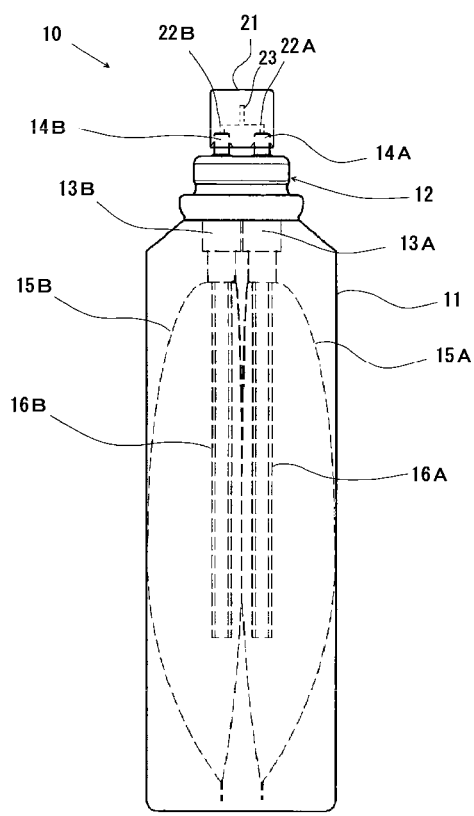
FIG. 1 is an explanatory view illustrating an example structure of a double-structure container used for a two-liquid mixing-type aerosol product of the present invention.

A two-liquid mixing-type aerosol product of the present invention has a double-structure container including a propellant filling space and two independent liquid concentrate filling spaces and having a discharging mechanism for simultaneously discharging the contents filled in these two liquid concentrate filling spaces as mists. In this double-structure container, the propellant filling space is filled with a propellant composed of a compressed gas, a first liquid concentrate filling space is filled with a first liquid concentrate composition, and a second liquid concentrate filling space is filled with a second liquid concentrate composition.

In the two-liquid mixing-type aerosol product of the present invention, the first liquid concentrate composition and the second liquid concentrate composition discharged simultaneously from the first liquid concentrate filling space and the second liquid concentrate filling space, respectively, are broken down into fine droplets by the discharging mechanism to form mists. In other words, the two-liquid mixing-type aerosol product of the present invention delivers a mixture of the first liquid concentrate composition and the second liquid concentrate composition as a discharge material in the form of mist.

In the two-liquid mixing-type aerosol product of the present invention, the first liquid concentrate composition is a liquid that contains a first component in a first medium with the first component capable of being dissolved in the first medium. On the other hand, the second liquid concentrate composition is a liquid that contains a second component in a second medium with the second component capable of being dissolved in the second medium and that is immiscible with the first liquid concentrate composition. In other words, the first liquid concentrate composition and the second liquid concentrate composition are immiscible with each other and each contain one of two liquids (specifically, the first medium and the second medium) as a medium for an active ingredient to be dissolved in each liquid.

The first medium and the first component that constitute the first liquid concentrate composition and the second medium and the second component that constitute the second liquid concentrate composition are appropriately selected according to, for example, the intended use of the two-liquid mixing-type aerosol product of the present invention.

Specific suitable examples of the two-liquid mixing-type aerosol product of the present invention include the examples (1) to (3) described below.

(1) In a first specific example, the first liquid concentrate composition contains a first component composed of a water-soluble component in a first medium including water as a main component. The second liquid concentrate composition contains a second component composed of an oil-soluble component in a second medium composed of an oil medium immiscible with water.

(2) In a second specific example, the first liquid concentrate composition contains a first component composed of an alcohol-soluble component in a first medium including an alcohol as a main component. The second liquid concentrate composition contains a second component composed of an oil-soluble component in a second medium composed of an oil medium immiscible with the alcohol that constitutes the first medium.

(3) In a third specific example, the first liquid concentrate composition contains a first component composed of an oil-soluble component in a first medium composed of an oil medium. The second liquid concentrate composition contains a second component composed of an oil-soluble component in a second medium composed of an oil medium immiscible with the oil medium that constitutes the first medium. The oil-soluble component that constitutes the first component is soluble in the oil medium that constitutes the first medium but is insoluble in the oil medium that constitutes the second medium. The oil-soluble component that constitutes the second component is soluble in the oil medium that constitutes the second medium but is insoluble in the oil medium that constitutes the first medium.

The two-liquid mixing-type aerosol product of the present invention is not limited to the examples (1) to (3) described above, and other examples may be employed. For example, in the two-liquid mixing-type aerosol product of the present invention, the first medium constituting the first liquid concentrate composition may be miscible with the second medium constituting the second liquid concentrate composition as long as the first liquid concentrate composition and the second liquid concentrate composition are immiscible with each other.

Hereinafter, an example of the two-liquid mixing-type aerosol product of the present invention will be described in detail.

In this example of the two-liquid mixing-type aerosol product, the first liquid concentrate composition is a liquid that contains a first component composed of an oil-insoluble component (specifically, a water-soluble component and an alcohol-soluble component) in a first medium composed of a non-oil medium (specifically, water and an alcohol). The second liquid concentrate composition is a liquid that contains a second component composed of an oil-soluble component in a second medium composed of an oil medium (specifically, a liquid oil) immiscible with water or an alcohol.

First Liquid Concentrate Composition:

The first liquid concentrate composition is a liquid that contains a first component composed of a water-soluble component in a first medium including water as a main component and optionally including an alcohol or the like. Alternatively, the first liquid concentrate composition is a liquid that contains a first component composed of an alcohol-soluble component in a first medium including an alcohol as a main component and optionally including water or the like.

As water constituting the first medium in the first liquid concentrate composition, purified water or ion-exchanged water is used.

As an alcohol constituting the first medium, ethanol or the like is used.

The content ratio of the first medium may preferably be 80.0% to 99.9% by mass per 100% by mass of the first liquid concentrate composition.

If the content ratio of the first medium is too high, the first component may not be present in a sufficient proportion.

If the content ratio of the first medium is too low, it is difficult to form the discharge material into a mist. Particularly for application to the human body, the comfort during use may not be obtained.

The first component, which is an essential component of the first liquid concentrate composition, serves as an active ingredient and is targeted for application.

The first component is not necessarily an active ingredient associated with the intended use of the two-liquid mixing-type aerosol product and may be, for example, an auxiliary for a main active ingredient, or a secondary active ingredient.

In the first liquid concentrate composition, the first component composed of an oil-insoluble component may preferably be at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an anti-pruritic component, a hair growth component and a deodorant component.

Examples of the whitening component include arbutin, tranexamic acid, kojic acid, hydroquinone, vitamin C and a vitamin C derivative.

Examples of the antioxidant component include polyphenol.

Examples of the anti-wrinkle component include glycerol and hyaluronic acid.

Examples of the film forming component include polyvinyl alcohol, polyvinylpyrrolidone and cationized cellulose.

Examples of the moisturizing component include amino acids, urea, sodium pyrrolidone carboxylate, hyaluronic acid, glycerol and polyethylene glycol.

Examples of the sterilizing component include benzalkonium chloride, benzethonium chloride, chlorhexidine hydrochloride and hinokitiol.

Examples of the ultraviolet absorbing component include phenylbenzimidazole sulfonic acid.

Examples of the astringent component include citric acid, succinic acid, tannic acid, hamamelis water, aloe and zinc sulfocarbolate.

Examples of the anti-inflammatory component include dipotassium glycyrrhizinate, an aloe extraction liquid (aloe extract) and a perilla extract.

Examples of the stratum corneum peeling component include salicylic acid, lactic acid, sulfur and resorcin.

Examples of the antipruritic component include diphenhydramine hydrochloride and chlorpheniramine maleate.

Examples of the hair growth component include a swertia herb extract, adenosine, calcium pantothenate and acetyl-pantothenyl ethyl ether.

Examples of the deodorant component include a green tea extract and alum.

The content ratio of the first component may preferably be 0.1% to 20% by mass per 100% by mass of the first liquid concentrate composition.

If the content ratio of the first component is too high, the first component may not be dissolved well in the first liquid concentrate composition.

If the content ratio of the first component is too low, the effect of the first component may not be exerted sufficiently.

The first liquid concentrate composition may contain optional components if necessary, in addition to the first medium (non-oil medium) and the first component (oil-insoluble component), which are essential components.

Examples of the optional components include a preservative, a coloring agent and a flavoring agent. A surfactant can also be used as an optional component.

The first liquid concentrate composition constituted by the essential components and the optional components as described above has a viscosity of 1 to 1000 mPa·s, preferably 1 to 500 mPa·s at a temperature of 20° C.

If the viscosity of the first liquid concentrate composition is too high, it is difficult to discharge the first liquid concentrate composition as a mist. In addition, the first liquid concentrate composition may not be discharged in a desired amount associated with the amount of the second liquid concentrate composition discharged.

Second Liquid Concentrate Composition:

The second liquid concentrate composition is a liquid that contains a second component composed of an oil-soluble component in a second medium composed of an oil medium immiscible with the non-oil medium that constitutes the first medium in the first liquid concentrate composition.

As the oil medium that constitutes the second medium, which is an essential component of the second liquid concentrate composition, a liquid oil that is in the form of liquid at room temperature is used.

The liquid oil that constitutes the second medium may preferably be at least one selected from the group consisting of a hydrocarbon compound, an ester compound, a silicone compound, an oil or fat, and a higher alcohol.

Examples of the hydrocarbon compound include kerosene, gas oil, mineral oil, squalane, liquid paraffin and light isoparaffin.

Examples of the ester compound include fatty acid esters, such as isopropyl myristate, butyl myristate, isocetyl myristate, octyldodecyl myristate, butyl stearate, ethylhexyl stearate, isopropyl isostearate, isopropyl palmitate, ethylhexyl palmitate, ethyl linoleate, butyloctyl salicylate, cetyl ethylhexanoate and ethyl olivate (ethyl oleate); polyhydric alcohol fatty acid esters, such as triethylhexanoin, propylene glycol monocaprylate, propylene glycol dicaprylate, trimethylolpropane triethylhexanoate, trimethylolpropane triisostearate and caprylic/capric triglyceride; and polybasic acid esters, such as diisopropyl adipate, diisopropyl sebacate and diethyl sebacate.

Examples of the silicone compound include dimethicone, cyclopentasiloxane and caprylyl methicone.

Examples of the oil or fat include vegetable oils and fats, such as white birch oil, rosehip oil, jojoba oil, chaulmoogra oil, sunflower oil, grape seed oil, avocado oil, hazelnut oil, camellia oleifera seed oil, broccoli seed oil, babasu oil, baobab oil, croton oil, olive oil, coffee bean oil, castor oil, rice bran oil, palm oil, palm kernel oil, tung oil, peach kernel oil, cherry oil, cranberry seed oil, jatropha curcas oil, shortening, cooking oil, refined rapeseed oil, perilla oil, pecan nut oil, pistachio oil, perilla seed oil, *Torreya nucifera* seed oil, apricot kernel oil, akebia oil, corn oil, stillingia oil, macadamia nut oil, linseed oil, coconut oil, sea buckthorn, cottonseed oil, hempseed oil, grape oil, poppyseed oil, mustard oil, camellia oil, wheat germ oil, evening primrose oil, peanut oil, pumpkinseed oil, laurel oil, safflower oil, argan oil, meadowfoam oil, marula oil, pomegranate seed oil, coconut oil, neem oil, soybean oil, kiwifruit seed oil, mongongo oil and walnut oil; and animal oils and fats, such as lanolin, horse oil, mink oil and squalene.

Examples of the higher alcohol include hexyldecanol, isostearyl alcohol, octyldodecanol, decyltetradecanol and oleyl alcohol.

The content ratio of the second medium may preferably be 40.0% to 99.9% by mass per 100% by mass of the second liquid concentrate composition.

If the content ratio of the second medium is too high, the second component may not be present in a sufficient ratio. Particularly for application to the human body, the discharge material may cause sticky feeling and may fail to provide comfort during use.

If the content ratio of the second medium is too low, the second component may not be dissolved well in the second liquid concentrate composition.

The second component, which is an essential component of the second liquid concentrate composition, is a substance insoluble in a non-oil medium. The second component serves as an active ingredient and is targeted for application.

The second component is not necessarily an active ingredient associated with the intended use of the two-liquid mixing-type aerosol product and may be, for example, an auxiliary for a main active ingredient, or a secondary active ingredient.

In the second liquid concentrate composition, the second component composed of an oil-soluble component may preferably be at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an antipruritic component, a hair growth component and a deodorant component.

Examples of the antioxidant component include astaxanthin and vitamin E.

Examples of the anti-wrinkle component include retinol and retinoic acid.

Examples of the film forming component include nitrocellulose, polymeric silicone and silicone resin.

Examples of the moisturizing component include vaseline.

Examples of the sterilizing component include piroctone olamine and isopropylmethyl phenol.

Examples of the ultraviolet absorbing component include ethylhexyl methoxycinnamate, 2-ethylhexyl p-dimethylaminobenzoate, octocrylene, ethylhexyl triazone, oxybenzone, t-butyl methoxydibenzoylmethane, diethylamino hydroxydibenzoyl hexyl benzoate, bis-ethylhexyloxyphenol methoxyphenyl triazine and methylene bis-benzotriazolyl tetramethylbutylphenol.

Examples of the cooling component include menthol, menthyl lactate, mentha oil, peppermint oil, camphor, thymol and methyl salicylate.

Examples of the warming component include capsaicin.

Examples of the anti-inflammatory component include glycyrrhetinic acid and azulene.

Examples of the antipruritic component include camphor and menthol.

The content ratio of the second component may preferably be 0.1% to 60% by mass per 100% by mass of the second liquid concentrate composition.

If the content ratio of the second component is too high, the second component may not be dissolved well in the second liquid concentrate composition.

If the content ratio of the second component is too low, the effect of the second component may not be exerted sufficiently.

The second liquid concentrate composition may contain optional components if necessary, in addition to the second medium (liquid oil) and the second component (oil-soluble component), which are essential components.

Examples of the optional components include an alcohol such as ethanol. A surfactant can also be used as an optional component.

The second liquid concentrate composition constituted by the essential components and the optional components as described above has a viscosity of 1 to 1000 mPa·s, preferably 1 to 500 mPa·s at a temperature of 20° C.

If the viscosity of the second liquid concentrate composition is too high, it is difficult to discharge the second liquid concentrate composition as a mist. In addition, the second liquid concentrate composition may not be discharged in a desired amount associated with the amount of the first liquid concentrate composition discharged.

Propellant:

A compressed gas is used as a propellant.

Examples of the compressed gas include nitrous oxide gas, nitrogen gas, carbon dioxide gas and a mixture of these gases.

This propellant is not discharged from the propellant filling space into the outside of the double-structure container along with simultaneous discharge of the first liquid concentrate composition and the second liquid concentrate composition.

The propellant may preferably be enclosed such that the pressure applied when the double-structure container is filled with the propellant is 0.3 to 1.2 MPa at 25° C.

If the pressure applied when the double-structure container is filled with the propellant (product inner pressure) is too high or too low, in both cases, the contents may not be sprayed in favorable conditions.

Double-Structure Container:

The double-structure container of the two-liquid mixing-type aerosol product of the present invention includes a propellant filling space to be filled with a propellant, a first liquid concentrate filling space to be filled with a first liquid concentrate composition, and a second liquid concentrate filling space to be filled with a second liquid concentrate composition. The double-structure container further includes a discharging mechanism for simultaneously discharging, as mists, the first liquid concentrate composition and the second liquid concentrate composition from the first liquid concentrate filling space and the second liquid concentrate filling space, respectively.

Figure 2:
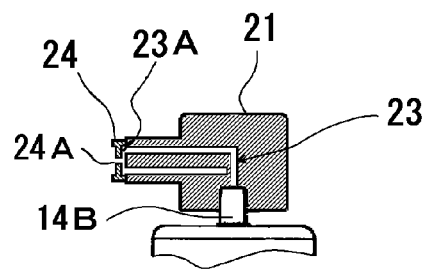
FIG. 2 is a sectional view illustrating a cross section of an actuator in the double-structure container in FIG. 1.

Specific examples of the double-structure container according to the present invention include the following container illustrated in FIG. 1 and FIG. 2.

FIG. 1 is an explanatory view illustrating an example structure of the double-structure container used for the two-liquid mixing-type aerosol product of the present invention. FIG. 2 is a sectional view illustrating the cross section of an actuator in the double-structure container in FIG. 1.

This double-structure container 10 includes a pressure resistant container 11 made of metal and provided with an aerosol valve 12. The pressure resistant container 11 is provided thereinside with a first inner bag 15A that is formed of, for example, an aluminum laminated film and that defines a first liquid concentrate filling space to be filled with the first liquid concentrate composition, and a second inner bag 15B that is formed of, for example, an aluminum laminated film and that defines a second liquid concentrate filling space to be filled with the second liquid concentrate composition. In the pressure resistant container 11, a propellant filling space to be filled with the propellant is formed from a gap defined by the pressure resistant container 11, the first inner bag 15A, and the second inner bag 15B. The aerosol valve 12 is provided with a first stem 14A and a second stem 14B each having a stem passage inside. The first stem 14A and the second stem 14B are disposed to be movable up and down inside a first housing 13A and a second housing 13B, respectively. A common actuator 21 is disposed on the upper ends of the first stem 14A and the second stem 14B.

In the example illustrated in the figure, a reference character 16A denotes a first dip tube in communication with the stem passage in the first stem 14A at the lower end of the first housing 13A. The first dip tube 16A extends inside the first inner bag 15A toward the bottom of the pressure resistant container 11. A reference character 16B denotes a second dip tube in communication with the stem passage in the second stem 14B at the lower end of the second housing 13B. The second dip tube 16B extends inside the second inner bag 15B toward the bottom of the pressure resistant container 11.

In FIG. 1, the components located inside the pressure resistant container 11 and the actuator 21 are drawn with broken lines.

The common actuator 21 contains a first actuator passage 22A in communication with the stem passage in the first stem 14A, a second actuator passage 22B in communication with the stem passage in the second stem 14B, and an L-shaped mixing space 23 in communication with, at its end, the first actuator passage 22A and the second actuator passage 22B and in communication with, at its another end, a discharge port 24A of a jet port-forming member 24. The mixing space 23 includes a swirl passage 23A through which the first liquid concentrate composition and the second liquid concentrate composition are passed and broken down into fine droplets.

The actuator 21 common to the first stem 14A for the first inner bag 15A and the second stem 14B for the second inner bag 15B is provided accordingly so as to form the discharging mechanism for simultaneously discharging, as mists, the first liquid concentrate composition filled in the first inner bag 15A and the second liquid concentrate composition filled in the second inner bag 15B from the first inner bag 15A and the second inner bag 15B, respectively.

In the double-structure container 10 having such a structure, the first inner bag 15A is filled with the first liquid concentrate composition, the second inner bag 15B is filled with the second liquid concentrate composition, and the propellant filling space is filled with a propellant. The inside of the pressure resistant container 11 is always pressurized with the propellant accordingly. Therefore, when the actuator 21 is actuated (depressed), the pressure of the propellant shrinks the first inner bag 15A and the second inner bag 15B, which causes the first liquid concentrate composition and the second liquid concentrate composition to be discharged simultaneously from the first inner bag 15A and the second inner bag 15B, respectively. As a result, a mixture of the first liquid concentrate composition and the second liquid concentrate composition is discharged as a mist from the discharge port 24A of the actuator 21.

Specifically, while the actuator 21 is not actuated or depressed in the double-structure container 10 filled with the first liquid concentrate composition, the second liquid concentrate composition, and the propellant, the first stem 14A and the second stem 14B are being pushed up to block the stem passage in the first stem 14A and the stem passage in the second stem 14B from the inside of the pressure resistant container 11. While the actuator 21 is actuated or depressed, the first stem 14A and the second stem 14B are pushed down, so that the stem passage in the first stem 14A and the stem passage in the second stem 14B simultaneously communicate with the inside of the pressure resistant container 11. The first liquid concentrate composition in the first inner bag 15A and the second liquid concentrate composition in the second inner bag 15B are discharged simultaneously through the fluid passages formed by the first dip tube 16A and the second dip tube 16B, respectively. The first liquid concentrate composition and the second liquid concentrate composition thus simultaneously discharged reach the mixing space 23 through the stem passage in the first stem 14A and the stem passage in the second stem 14B and through the first actuator passage 22A and the second actuator passage 22B, respectively. The first liquid concentrate composition and the second liquid concentrate composition are mixed in the mixing space 23, further broken down into fine droplets while passing through the swirl passage 23A, and discharged from the discharge port 24A as mists.

In the double-structure container having the structure described above, the discharging mechanism enables the first liquid concentrate composition filled in the first liquid concentrate filling space and the second liquid concentrate composition filled in the second liquid concentrate filling space to be discharged simultaneously as mists. The discharging mechanism further enables the amount of the first liquid concentrate composition discharged from the first liquid concentrate filling space and the amount of the second liquid concentrate composition discharged from the second liquid concentrate filling space to be controlled at an appropriate quantitative ratio, specifically, so as to be substantially the same.

In the two-liquid mixing-type aerosol product of the present invention, the mixing ratio of the first liquid concentrate composition discharged from the first liquid concentrate filling space to the second liquid concentrate composition discharged from the second liquid concentrate filling space (the mass of the first liquid concentrate composition:the mass of the second liquid concentrate composition) may preferably be from 0.8:1.2 to 1.2:0.8.

In other words, the amount of the first liquid concentrate composition discharged from the first liquid concentrate filling space and the amount of the second liquid concentrate composition discharged from the second liquid concentrate filling space each may preferably fall within a range of ±20% of the mean of the amounts of the first liquid concentrate composition discharged and the second liquid concentrate composition discharged.

The mixing ratio (the mass of the first liquid concentrate composition:the mass of the second liquid concentrate composition) can be controlled within the above-described range by setting, for example, the viscosity of the first liquid concentrate composition at a temperature of 20° C. to 1 to 1,000 mPa·s, and the viscosity of the second liquid concentrate composition at a temperature of 20° C. to 1 to 1,000 mPa·s.

If the mixing ratio (the mass of the first liquid concentrate composition:the mass of the second liquid concentrate composition) is out of the above-described range, the amount of the first liquid concentrate composition discharged from the first liquid concentrate filling space is significantly different from the amount of the second liquid concentrate composition discharged from the second liquid concentrate filling space. As a result, the discharge material may not provide desired effects or comfort during use when it is applied to the human body.

The two-liquid mixing-type aerosol product of the present invention described above is produced by filling the first liquid concentrate filling space and the second liquid concentrate filling space in the double-structure container with the first liquid concentrate composition and the second liquid concentrate composition, respectively, and filling the propellant filling space with the propellant.

The two-liquid mixing-type aerosol product of the present invention has a double-structure container including a discharging mechanism for simultaneously discharging the contents filled in two liquid concentrate filling spaces as mists. One of two liquid concentrate filling spaces is filled with the first liquid concentrate composition having a particular viscosity, whereas the other is filled with the second liquid concentrate composition having a particular viscosity and being immiscible with the first liquid concentrate composition.

Therefore, there is no need to use a surfactant for emulsifying the first liquid concentrate composition and the second liquid concentrate composition. The first liquid concentrate composition and the second liquid concentrate composition both have a large degree of freedom in formulation design, and high formulation stability is obtained.

Furthermore, the first liquid concentrate composition and the second liquid concentrate composition can be discharged simultaneously in appropriate amounts from two liquid concentrate filling spaces in the double-structure container. Therefore, the first liquid concentrate composition and the second liquid concentrate composition can always be mixed at a constant quantitative ratio, so that there is no possibility that the amount of one liquid concentrate composition discharged is much larger than the amount of another liquid concentrate composition discharged. In addition, the discharge material can be applied to an application site thinly and uniformly. As a result, desired effects are always obtained at an application site, that is, a discharge material having a desired composition can be applied in a desired amount by simply operating the discharging mechanism, specifically, for example, only depressing the actuator once (one push) to discharge the first liquid concentrate composition and the second liquid concentrate composition.

Therefore, the two-liquid mixing-type aerosol product of the present invention has high formulation stability and easily enables a mixture containing the first liquid concentrate composition and the second liquid concentrate composition at a desired ratio to be uniformly applied to an application site in a desired amount. Furthermore, the two-liquid mixing-type aerosol product of the present invention can prevent or reduce occurrence of sticky feeling caused by addition of a surfactant and can thus provide comfort during use when it is applied to the human body.

In the two-liquid mixing-type aerosol product of the present invention, active ingredients that are considered difficult to use in combination in the same stock solution from the viewpoint of formulation stability and the like can be used together without any undesirable effects. Specifically, vitamin C (water-soluble component) and vitamin E (oil-soluble component) can be used in combination, and an aloe extract (water-soluble component) and ethylhexyl methoxycinnamate (oil-soluble component) can be used in combination.

In the two-liquid mixing-type aerosol product of the present invention, a non-flammable compressed gas is used as a propellant for the first liquid concentrate composition and the second liquid concentrate composition. The use of the non-flammable compressed gas provides high safety irrespective of the operation environment and eliminates the risk of an explosion accident in discarding the double-structure container.

Moreover, the long-term storage stability can be obtained because neither the first liquid concentrate composition nor the second liquid concentrate composition is exposed to the air outside the container during application.

In the two-liquid mixing-type aerosol product of the present invention, the discharge material is obtained as a mist, which eliminates the need to mix the first liquid concentrate composition and the second liquid concentrate composition at an application site or the like and also eliminates the need to spread the coating of the applied discharge material. It is thus easy to apply the discharge material.

Such a two-liquid mixing-type aerosol product of the present invention can be used in various applications, such as products for the human body, daily necessaries, and food. Since the two-liquid mixing-type aerosol product of the present invention exerts comfort during use when it is applied to the human body, this product can preferably be used particularly for the human body.

Examples of the product for the human body include whitening agents, beauty products, sunscreens, makeup bases, skin protective agents, moisturizers, hair styling products, hair waxes, hair treatments, hair growth agents, massaging agents and shaving agents.

EXAMPLES

Examples of the present invention will be described below, but the present invention is not limited by these.

Example 1: Production of Two-Liquid Mixing-Type Aerosol Product for Use as Beauty Product Preparation of First Liquid Concentrate Composition:
A first liquid concentrate composition was prepared by mixing the components described below.
The viscosity of the obtained first liquid concentrate composition at a temperature of 20° C. was measured using a BM-type rotary viscometer (rotor No. 1, 60 rpm, after 1 minute) and found to be 50 mPa·s.
Constituents of First Liquid Concentrate Composition:
Water: 93.96% by mass
Sodium hyaluronate: 0.01% by mass
Vitamin C derivative (disodium ascorbate sulfate): 0.40% by mass
1,3-Butylene glycol: 5.00% by mass
Phenoxyethanol: 0.30% by mass
Citric acid: 0.02% by mass
Sodium citrate: 0.01% by mass
"Rosemary extract BG-J" (manufactured by Maruzen Pharmaceuticals Co. Ltd.): 0.10% by mass
"Chamomile extract BG-J" (manufactured by Maruzen Pharmaceuticals Co. Ltd.): 0.10% by mass
"Paeoniae radix extract BG-JC" (manufactured by Maruzen Pharmaceuticals Co. Ltd.): 0.10% by mass
Total: 100.00% by mass
Preparation of Second Liquid Concentrate Composition:
A second liquid concentrate composition was prepared by mixing the components described below.
The viscosity of the obtained second liquid concentrate composition at a temperature of 20° C. was measured using a BM-type rotary viscometer (rotor No. 2, 60 rpm, after 1 minute) and found to be 100 mPa·s.
Constituents of Second Liquid Concentrate Composition:
Mineral oil: 76.30% by mass
Vitamin E (tocopherol acetate): 0.20% by mass
Dimethicone: 2.00% by mass
Cyclopentasiloxane: 20.00% by mass
Jojoba oil: 0.50% by mass
Olive oil: 0.50% by mass
Squalane: 0.50% by mass
Total: 100.00% by mass
Production of Two-Liquid Mixing-Type Aerosol Product:
A two-liquid mixing-type aerosol product for use as a beauty product was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the product inner pressure in the double-structure container was 0.7 MPa at 25° C. In this two-liquid mixing-type aerosol product, the first liquid concentrate composition is a liquid cosmetic formulation for water-based beauty products in which a first medium contains water and which contains a vitamin C derivative (whitening component) as a first component composed of a water-soluble component. The second liquid concentrate composition is a liquid cosmetic formulation for oil-based beauty products in which a second medium contains a mineral oil and cyclopentasiloxane and which contains vitamin E as a second component composed of an oil-soluble component.

Example 2: Production of Two-Liquid Mixing-Type Aerosol Product for Use as Sunscreen Preparation of First Liquid Concentrate Composition:
A first liquid concentrate composition was prepared by mixing the components described below.
The viscosity of the obtained first liquid concentrate composition at a temperature of 20° C. was measured using a BM-type rotary viscometer (rotor No. 1, 60 rpm, after 1 minute) and found to be 50 mPa·s.
Constituents of First Liquid Concentrate Composition:
Purified water: 97.7% by mass
Glycerol: 2.00% by mass
Aloe extract: 0.1% by mass
Methylparaben: 0.2% by mass
Total: 100.0% by mass
Preparation of Second Liquid Concentrate Composition:
A second liquid concentrate composition was prepared by mixing the components described below.
The viscosity of the obtained second liquid concentrate composition at a temperature of 20° C. was measured using a BM-type rotary viscometer (rotor No. 1, 60 rpm, after 1 minute) and found to be 80 mPa·s.
Constituents of Second Liquid Concentrate Composition:
Ethylhexyl methoxycinnamate: 10.0% by mass
Ethylhexyl palmitate: 10.0% by mass
Caprylyl methicone: 5.0% by mass
Cyclopentasiloxane: 35.0% by mass
Ethanol: 40.0% by mass
Total: 100.0% by mass
Production of Aerosol Product:
A two-liquid mixing-type aerosol product for use as a sunscreen was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the product inner pressure in the double-structure container was 0.7 MPa at 25° C. In this two-liquid mixing-type aerosol product, the first liquid concentrate composition is a liquid cosmetic formulation for water-based lotions in which a first medium contains water and which contains an aloe extract (anti-inflammatory component) as a first component composed of a water-soluble component. The second liquid concentrate composition is a liquid cosmetic formulation for oil-based sunscreens in which a second medium contains ethylhexyl palmitate, caprylyl methicone, and cyclopentasiloxane and which contains ethylhexyl methoxycinnamate (ultraviolet absorbing component) as a second component composed of an oil-soluble component.

The two-liquid mixing-type aerosol products according to Example 1 and Example 2 were found to provide comfort during use without sticky feeling when they were applied to the skin just after production.

The two-liquid mixing-type aerosol products according to Example 1 and Example 2 were also found to deliver a mist of discharge material that provides functions (effects) attributed to the first component (water-soluble component) and the second component (oil-soluble component) even after the products had been stored for a long time over one month in an environment at a temperature of 45° C.

REFERENCE SIGNS LIST 10 double-structure container
11 pressure resistant container
12 aerosol valve
13A first housing
13B second housing
14A first stem
14B second stem
15A first inner bag
15B second inner bag
16A first dip tube
16B second dip tube
21 actuator
22A first actuator passage
22B second actuator passage
23 mixing space
23A swirl passage
24 jet port-forming member
24A discharge port

The invention claimed is:
1. A two-liquid mixing-type aerosol apparatus comprising:
a single pressure resistant container;
a first liquid concentrate flexible container disposed inside the single pressure resistant container;
a second liquid concentrate flexible container disposed inside the single pressure resistant container and separate from the first liquid concentrate flexible container;
a propellant filled space disposed inside the single pressure resistant container and exterior to the first and second liquid concentrate flexible containers;
discharging mechanism mounted on the single pressure resistant container for simultaneously discharging contents of the first and second liquid concentrate containers;
a propellant comprising a compressed gas in the propellant filled space;
a first liquid concentrate composition comprising a first liquid that includes a first component in a first medium with the first component dissolved in the first medium, the first liquid concentrate composition in the first liquid concentrate flexible container; and
a second liquid concentrate composition comprising a second liquid that includes a second component in a second medium with the second component dissolved in the second medium, the second liquid concentrate composition in the second liquid concentrate flexible container, wherein
the second liquid concentrate composition is immiscible with the first liquid concentrate composition,
neither the first liquid concentrate composition nor the second liquid concentrate composition contains a surfactant for emulsifying,
the first liquid concentrate composition and the second liquid concentrate composition each have a viscosity from 1 to 1000 mPa·s at a temperature of 20° C.,
the discharging mechanism is adapted to break the first liquid concentrate composition and the second liquid concentrate composition down into fine droplets and discharging the first and second liquid concentrate compositions together as mists,
the discharging mechanism comprises a first stem in communication with the first liquid concentrate flexible container, a second stem in communication with the second liquid concentrate flexible container, and a common actuator thereto,
the common actuator contains a first actuator passage in communication with the first stem, a second actuator passage in communication with the second stem, and a mixing space in communication with, at its end, the first actuator passage and the second actuator passage and in communication with, at its another end, a discharge port;
the mixing space contains a swirl passage through which the first liquid concentrate composition and the second liquid concentrate composition are passed and broken down into fine droplets; and
the first liquid concentrate composition in the first liquid concentrate flexible container and the second liquid concentrate composition in the second liquid concentrate flexible container are simultaneously discharged as mists from the discharge port.

2. The two-liquid mixing-type aerosol apparatus according to claim 1, wherein
the first component comprises an oil-soluble component or an oil-insoluble component, and the first medium comprises an oil medium or a non-oil medium, and
the second liquid concentrate composition is an oil product, the second component comprises an oil-soluble component, and the second medium comprises an oil medium.

3. The two-liquid mixing-type aerosol apparatus according to claim 2, wherein
the oil medium comprises at least one selected from the group consisting of a hydrocarbon compound, an ester compound, a silicone compound, an oil or fat, and a higher alcohol.

4. The two-liquid mixing-type aerosol apparatus according to claim 2, wherein
the oil-insoluble component comprises at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an antipruritic component, a hair growth component and a deodorant component.

5. The two-liquid mixing-type aerosol apparatus according to claim 2, wherein
the oil-soluble component comprises at least one selected from the group consisting of a whitening component, an antioxidant component, an anti-wrinkle component, a film forming component, a moisturizing component, a sterilizing component, an ultraviolet absorbing component, a cooling component, an astringent component, a warming component, an anti-inflammatory component, a stratum corneum peeling component, an antipruritic component, a hair growth component and a deodorant component.

6. The two-liquid mixing-type aerosol apparatus according to claim 1, wherein
a mixing ratio of a first mass of the first liquid concentrate composition to a second mass of the second liquid concentrate composition discharged from the discharging mechanism is from 0.8:1.2 to 1.2:0.8.

7. The two-liquid mixing-type aerosol product according to claim 1, wherein the two-liquid mixing-type aerosol apparatus is adapted to be used for a human body.

* * * * *